(12) United States Patent
Koblish et al.

(10) Patent No.: US 9,023,030 B2
(45) Date of Patent: May 5, 2015

(54) COOLED ABLATION CATHETER DEVICES AND METHODS OF USE

(75) Inventors: Josef Koblish, Sunnyvale, CA (US); Leslie Oley, Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 756 days.

(21) Appl. No.: 12/247,619

(22) Filed: Oct. 8, 2008

(65) Prior Publication Data

US 2009/0093811 A1  Apr. 9, 2009

Related U.S. Application Data

(60) Provisional application No. 60/978,511, filed on Oct. 9, 2007.

(51) Int. Cl.
| | |
|---|---|
| *A61B 18/18* | (2006.01) |
| *A61N 1/06* | (2006.01) |
| *A61B 18/14* | (2006.01) |
| *A61B 18/00* | (2006.01) |

(52) U.S. Cl.
CPC .............. *A61N 1/06* (2013.01); *A61B 18/1492* (2013.01); *A61B 2018/00821* (2013.01); *A61B 2218/002* (2013.01)

(58) Field of Classification Search
USPC ............................... 606/39, 40, 41, 42, 43, 49
See application file for complete search history.

(56) References Cited

U.S. PATENT DOCUMENTS

| | | | | |
|---|---|---|---|---|
| 3,911,928 A | * | 10/1975 | Lagergren ..................... 607/122 |
| 4,360,031 A | * | 11/1982 | White ........................... 607/120 |
| 4,532,924 A | * | 8/1985 | Auth et al. ...................... 606/50 |
| 5,122,137 A | * | 6/1992 | Lennox .......................... 606/40 |
| 5,318,014 A | * | 6/1994 | Carter ........................... 606/128 |
| 5,348,554 A | * | 9/1994 | Imran et al. ..................... 606/41 |
| 5,429,131 A | * | 7/1995 | Scheinman et al. ........... 600/374 |
| 5,462,521 A | * | 10/1995 | Brucker et al. ................. 604/20 |
| 5,584,872 A | * | 12/1996 | LaFontaine et al. .......... 607/116 |
| 5,643,197 A | * | 7/1997 | Brucker et al. ................. 604/20 |
| 5,688,267 A | * | 11/1997 | Panescu et al. ................. 606/41 |
| 5,792,140 A | * | 8/1998 | Tu et al. ......................... 606/41 |
| 5,800,432 A | * | 9/1998 | Swanson ........................ 606/49 |
| 5,836,875 A | * | 11/1998 | Webster, Jr. .................. 600/374 |
| 5,853,409 A | * | 12/1998 | Swanson et al. ............... 606/31 |
| 5,957,922 A | * | 9/1999 | Imran ............................ 606/41 |
| 6,030,379 A | * | 2/2000 | Panescu et al. ................. 606/34 |
| 6,053,912 A | * | 4/2000 | Panescu et al. ................. 606/40 |

(Continued)

FOREIGN PATENT DOCUMENTS

| | | |
|---|---|---|
| EP | 1 514 523 | 3/2005 |
| JP | 11506947 A | 6/1999 |

(Continued)

*Primary Examiner* — Nicholas Lucchesi
*Assistant Examiner* — William Carpenter
(74) *Attorney, Agent, or Firm* — Seager, Tufte & Wickhem, LLC (57) ABSTRACT

Discloses herein are ablative catheters and methods of use. The catheters can include a cooling chamber for circulating cooling fluid within the catheter tip to reduce hot spots within the catheter tip and/or to reduce the formation of coagulum. A proximal cooling chamber can be positioned proximally to a thermal mass for cooling a proximal portion of the catheter. In addition, or alternatively, a distal cooling chamber can be positioned for cooling a distal portion of the catheter tip. The cooling fluid can flow the ablative catheter in an open, closed, or open and closed loop.

10 Claims, 6 Drawing Sheets

(56) References Cited

U.S. PATENT DOCUMENTS

| | | | |
|---|---|---|---|
| 6,120,476 A * | 9/2000 | Fung et al. | 604/95.04 |
| 6,241,724 B1 * | 6/2001 | Fleischman et al. | 606/41 |
| 6,405,078 B1 * | 6/2002 | Moaddeb et al. | 604/21 |
| 6,569,162 B2 * | 5/2003 | He | 606/41 |
| 6,602,242 B1 * | 8/2003 | Fung et al. | 604/528 |
| 6,611,699 B2 * | 8/2003 | Messing | 600/372 |
| 6,662,034 B2 * | 12/2003 | Segner et al. | 600/373 |
| 7,077,842 B1 * | 7/2006 | Cosman | 606/41 |
| 7,097,641 B1 * | 8/2006 | Arless et al. | 606/20 |
| 7,311,708 B2 * | 12/2007 | McClurken | 606/50 |
| 7,507,237 B2 * | 3/2009 | Geistert | 606/41 |
| 7,857,809 B2 * | 12/2010 | Drysen | 606/41 |
| 7,918,851 B2 * | 4/2011 | Webster et al. | 606/41 |
| 2003/0004506 A1 * | 1/2003 | Messing | 606/41 |
| 2003/0164435 A1 * | 9/2003 | Flynn | 248/441.1 |
| 2004/0267106 A1 * | 12/2004 | Segner et al. | 600/374 |
| 2009/0093810 A1 * | 4/2009 | Subramaniam et al. | 606/41 |
| 2011/0009857 A1 * | 1/2011 | Subramaniam et al. | 606/33 |
| 2011/0060331 A1 * | 3/2011 | Ibrahim et al. | 606/41 |
| 2014/0205367 A1 * | 7/2014 | Sung | 403/192 |

FOREIGN PATENT DOCUMENTS

| | | |
|---|---|---|
| WO | WO9636860 A2 | 11/1996 |
| WO | WO 01/41664 | 6/2001 |
| WO | WO 2004/093703 | 11/2004 |

* cited by examiner

COOLED ABLATION CATHETER DEVICES AND METHODS OF USE

This application claims priority to Provisional Application Ser. No. 60/978,511 entitled "Cooled Ablation Catheter Devices and Methods of Use" filed Oct. 9, 2007, which is incorporated herein by reference.

BACKGROUND

Atrial fibrillation is a condition in the heart in which the generation of abnormal electrical signals causes irregular beatings of the heart. A proven protocol for successfully treating this condition is open heart surgery (sometimes referred to as the "maze" procedure) where several long (i.e. approximately 2-10 cm) lesions are created in the endocardium within the upper chambers of the heart ("atria"). These lesions block the flow of excess electrical impulses within the atria and allow the impulse from the sinus node to properly regulate heart contraction.

However, because open heart surgery is highly invasive and requires a lengthy patient recovery period, alternative methods for making lesions have been recently explored. One such alternative is the use of ablation catheters that includes one or more electrodes.

Typically, an ablation catheter is advanced into the heart via the patient's vessels. When the electrodes are placed in the desired position within the heart chamber, radio frequency ("RF") energy is supplied to the catheter thereby burning lesions into the endocardium.

Initial designs for ablation catheters generally comprised an elongated shaft with an electrode mounted at the distal end. Either point and linear lesions could be formed with these catheters by manipulating the placement of the tip. However, because of the tendency for the tip electrode to overheat and to lift off the tissue surface during ablation, creating suitable lesions using these catheters have been difficult.

New catheter designs attempted to mitigate these disadvantages. One improvement is the addition of a mechanism to cool the tip electrode during use to minimize the risk of embolism from overheated blood. Although these catheters mitigate some of the overheating problems, hotspots on the tip or in adjacent tissue may still develop.

Accordingly, while some conventional catheters are effective for cardiac ablation, further advances could be beneficial.

SUMMARY OF THE INVENTION

Described herein are devices, systems and methods for medical treatment and particularly for delivering ablative energy to target tissue while reducing the formation of coagulum and/or for minimizing the effects of biological debris on the delivery of energy to tissue. In one aspect, an ablation catheter having an ablative electrode tip is disclosed. The catheter can include a pathway or channel for delivery of cooling fluid to the ablative tip. Within the tip, cooling fluid can circulate in an open loop, closed loop, and/or open/closed loop configuration.

In one embodiment, the catheter is sized and shaped for vascular access and includes an elongate body extending between a proximal end and a distal end. The elongate body can include at least one inner fluid lumen and an electrode tip can be positioned proximate to the distal end of the catheter body. In one aspect, the tip includes an outer wall and an inner thermal mass having at least one fluid passageway therethrough. A cooling chamber, which is in fluid communication with the inner fluid lumen of the elongate body, can be positioned proximally to the thermal mass and adapted to cool a proximal portion of the electrode tip including the thermal mass.

In another aspect, the tip can further comprise multiple irrigation apertures in communication with the fluid passageway in the tip. Cooling fluid can flow into the proximal cooling chamber, through the thermal mass, and into the surrounding environment via the multiple irrigation apertures.

The cooling chamber, in one aspect, extends across substantially the entire width of the tip between the outer walls of the tip. The cooling chamber can be defined by a cavity at the proximate-most end of the tip that is bounded at its distal end by the thermal mass and is bounded at its proximal end by a portion of the tip and/or by a portion of the elongate catheter body.

In another aspect, the size and shape of the cooling chamber is adapted to cause fluid circulation within the cooling chamber. In one aspect, the cooling chamber has a greater cross-sectional area than the fluid inlet and/or outlet to the cooling chamber. In another aspect, a fluid ingress to the cooling chamber is offset from a fluid egress from the cooling chamber.

In one aspect, the thermal mass comprises a material having a high thermal conductivity. A temperature sensor can be positioned at least partially within the thermal mass. In another aspect, the thermal mass extends across substantially the full width of the tip with the exception of a cooling fluid flow path or flow paths extending therethrough. The cross-section of the fluid flow path or paths through the thermal mass can be less than the cross-sectional area of the cooling chamber. In one aspect, the size of the cooling chamber relative to the fluid flow path or paths in the thermal mass results in an increase in pressure and/or in fluid flow speed in the fluid flow path or paths relative to the cooling chamber.

The electrode tip can include multiple irrigation apertures for the delivery of cooling fluid to the environment surrounding the electrode tip. In one aspect, the irrigation apertures deliver fluid to the outer, distal surface of the tip. In another aspect, one or more of the multiple irrigation apertures is positioned distally of the temperature sensor, thermal mass, and/or cooling chamber.

In another embodiment, the catheter described herein further comprises a second cooling chamber positioned distally from the thermal mass. Cooling fluid can flow through the proximal cooling chamber, through the thermal mass, and then into the distal cooling chamber. In one aspect, irrigation apertures allow egress of the cooling fluid from the distal cooling chamber.

In one aspect, a cross-sectional width of the distal cooling chamber is greater than the fluid flow path or paths through the thermal mass. In another aspect, the fluid passageway through the thermal mass is sized and shaped to produce an increase in the fluid pressure within the fluid passageway or passageways in the thermal mass with respect to the proximal and/or distal cooling chambers.

In another embodiment described herein a catheter device is disclosed. The catheter can be sized and shaped for vascular access and include an elongate body extending between a proximal end and a distal end and having at least one inner fluid lumen. An electrode tip position proximate to the distal end of the catheter body can include an outer wall and an inner thermal mass having at least one fluid passageway therethrough. The tip can include a proximal cooling chamber in fluid communication with the inner fluid lumen of the elongate body and positioned proximally of the thermal mass and adapted to cool a proximal surface of the thermal mass, and a distal cooling chamber positioned distally of the thermal mass. A fluid path can extend from the proximal cooling chamber, through the at least one fluid passageway in the thermal mass, and into the distal cooling chamber. Cooling fluid can then exit the tip through multiple irrigation apertures in communication with the distal cooling chamber. The at least one passageway through the thermal mass can be sized and shaped to produce a pressure increase within the at least one fluid passageway with respect to the proximal or a distal cooling chamber.

In another embodiment of the catheter device described herein, an electrode tip includes combined open and closed loop cooling flow paths. In one aspect, the elongate body include a second fluid lumen for the removal of cooling fluid from the tip. For example, cooling fluid can flow through a first fluid lumen within the elongate body and into a proximal cooling chamber. After circulating through the proximal cooling chamber, at least a portion of the cooling fluid is then removed via the second fluid lumen. Cooling fluid not removed via the second fluid lumen flow can exit the tip via irrigation apertures. Thus, a portion of the fluid flows in a closed loop path (and is removed through the catheter body) and a portion of the fluid flows into the environment surrounding the distal tip in an open loop path. In one aspect, the open loop path includes a fluid pathway through a thermal mass and/or distal cooling chamber.

In one aspect, the open and closed loop flow paths are separate from one another. For example, cooling fluid can flow, via a first flow path, into a first cooling chamber, circulate therein, and then be removed. All of the cooling fluid can exit through the elongate body of the catheter without exiting via irrigation apertures into the surrounding environment. In a separate, second flow path, fluid can be delivered to multiple irrigation apertures and enter the environment surrounding the electrode tip. In one aspect, fluid within the first and second flow paths does not mix within the electrode tip.

Further described herein are methods of ablating tissue. One exemplary method includes the steps of providing a catheter having an electrode tip including an outer wall and an inner thermal mass having at least one fluid passageway therethrough, a proximal cooling chamber positioned proximally of the thermal mass and adapted to cool a proximal surface of the thermal mass, and a distal cooling chamber positioned distally of the thermal mass. The method can include delivering fluid into the proximal cooling chamber, then moving the fluid through the thermal mass and into the distal cooling chamber. In one aspect, fluid is then released into the surrounding environment via multiple irrigation apertures in communication with the distal cooling chamber.

It is to be understood that both the foregoing general description and the following detailed description are exemplary and explanatory only and are not restrictive of the invention, as claimed. In addition, structures and features described with respect to one embodiment can similarly be applied to other embodiments.

BRIEF DESCRIPTION OF THE DRAWINGS

The accompanying drawings, which are incorporated in and constitute a part of this specification, provide illustrative embodiments of the invention and, together with the description, serve to explain the principles of the invention.

DETAILED DESCRIPTION

Disclosed herein are cooled ablation catheters and methods of use. In general, the catheters include a flow path that provides cooling to a distal tip. The catheter can include an electrode tip having irrigation apertures for delivery of a cooling fluid to the environment surrounding the distal tip and/or to the surface of the distal tip. In addition, the electrode tip can comprise a proximal cooling chamber through which cooling fluid circulates prior to egress through the irrigation apertures. The proximal cooling chamber can reduce hotspots sometimes associated with conventional ablation catheters.

Figure 1:
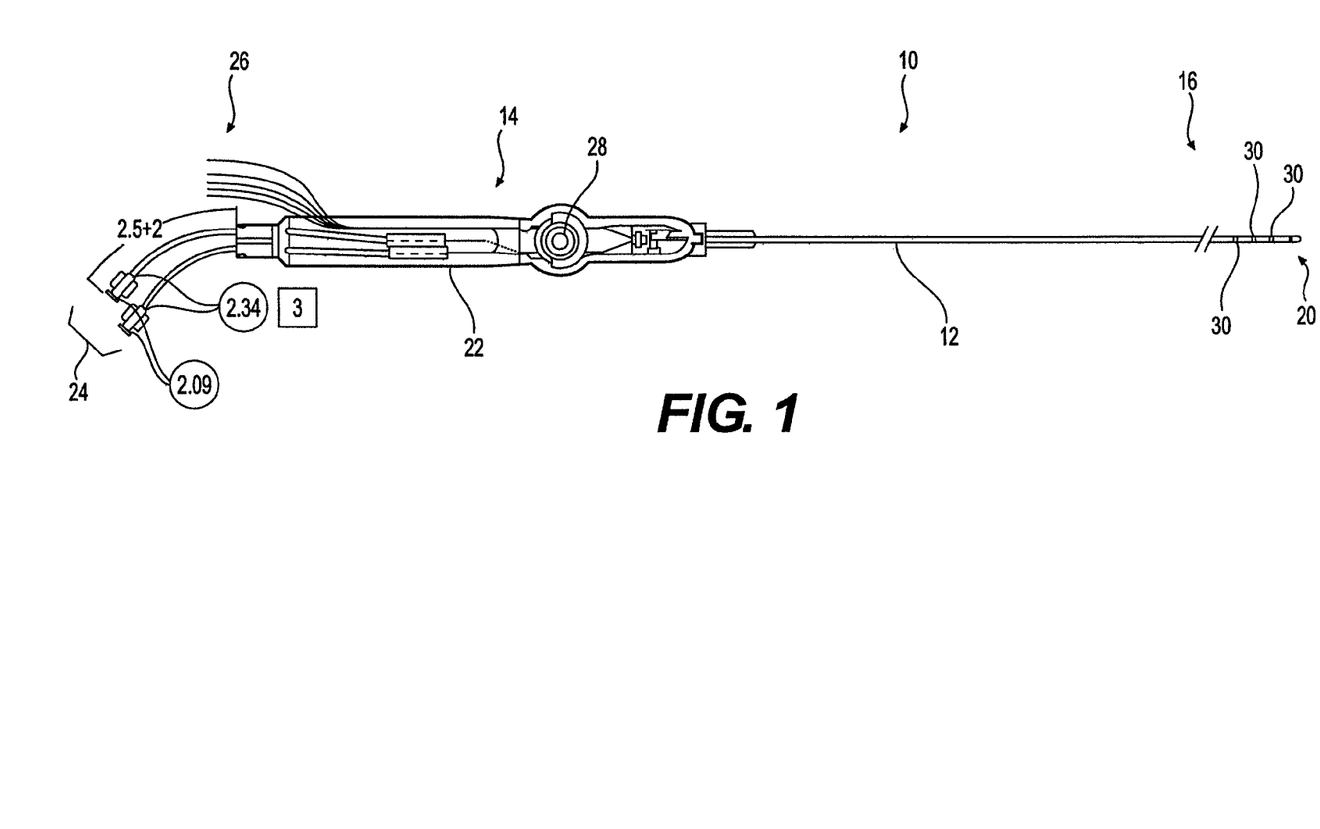
FIG. 1 is a partially transparent view of one exemplary embodiment of an ablation catheter described herein.

FIG. 1 provides a cut-away view of one exemplary embodiment of an ablation catheter device 10 for use with the distal tip structure described herein. Device 10 can include an elongate body 12 extending between a proximal section 14 and a distal section 16. The distal section includes an electrode tip 20 positioned to deliver ablative energy to tissue and is discussed in detail below.

In one aspect, the proximal portion of device 10 includes a handle 22 for grasping by a user. The handle can incorporate a variety of features to facilitate control of the catheter and/or mating of the catheter with a source of fluid, a source of ablative energy, a temperature display, sensors, and/or control software/hardware. In one aspect, handle 22 includes at least one fitting for mating with a source of cooling fluid and can include, two, three, or more than three ports 24 for receiving or expelling fluid. In addition, the catheter can include mating elements 26 for receiving and transmitting ablative energy to the distal tip. One skilled in the art will appreciate that a variety of catheter handle configurations are contemplated depending on the features of the catheter body 12, distal tip 20, and/or the intended use of device 10.

In another aspect, handle 22 can include a control mechanism 28 for directing movement of a distal portion of elongate body 12. Device 10 can include an articulating section of catheter body 12 that is controlled via the proximal control mechanism. In one aspect, a distal portion of the catheter body can be deflected or bent. The articulation section of the body can facilitate insertion of the catheter through a body lumen (e.g., vasculature) and/or placement of electrodes at a target tissue location. The articulation section can provide one or more degrees of freedom and permit up/down and/or left/right articulation. One skilled in the art will understand that the control mechanism and articulating portion of the catheter can include the variety of features associated with conventional articulating catheters.

Elongate body 12 can be defined by a flexible catheter body extending between handle 22 and distal section 16. In one embodiment, body 12 can house at least one fluid passageway for the transfer of cooling fluid to and/or from tip 20. In addition, body 12 can house electrical conductors (e.g., wires) for transmitting sensed signals and/or ablation energy. Still further, articulation mechanisms, such as, for example, pull wires can extend along body 12 to an articulation section of the device. One skilled in the art will appreciate that body 12 can represent the variety of know catheter structures for travel through a body cavity, such as, for example, a vascular lumen.

The distal section 16 of device 10 can include a portion of the catheter body and/or tip 20 comprising at least one electrode for delivering ablation energy, for sensing physiological signals, and/or for acting as a return electrode. In one aspect, multiple ring electrodes 30 are positioned around the distal portion of the catheter. The ring electrodes can permit sensing and/or mapping of cardiac signals. FIG. 1 illustrates three ring electrodes 30 positioned proximally from distal tip electrode 20. Any of the ring electrodes and/or tip electrode can be paired to sense physiological signals.

In addition to sensing, the distal portion of device 10 can delivery ablation energy in a bipolar and/or monopolar manner. For example, radio frequency, microwave, and/or other ablative energy can be delivered via distal tip 20. Ring electrode(s) 30 and/or a separate ground pad can act as a return electrode.

FIGS. 2A through 6 illustrate exemplary embodiments of distal tip 20. In one aspect, tip 20 is defined at least in part by an electrode for delivering ablative energy to target tissue. Tip 20 includes a flow path, indicated by arrows 21, for cooling the tip. As cooling fluid moves through tip 20, the fluid draws heat away from tip to control or reduce the temperature of the electrode. The reduced temperature can inhibit coagulum formation on device 10.

A build up of biological materials on the outer surface of the tip and/or in the area surrounding the tip can result in less effective energy transfer to the tissue. This effect can be seen as a rise in impedance and a corresponding increase in tissue heating and/or charring immediately adjacent to the tip. Cooling of the tip can permit more efficient energy transfer to tissue and allow larger lesion sizes for a give electrode mass or for a given amount of ablative energy transmitted to the tip.

In one aspect, the flow path directs cooling fluid through tip 20 to the outer surface of tip 20. Movement of fluid, such as cooling fluid, around tip 20 while the device is in contact with tissue, and energy is delivered to the tissue, can inhibit impedance rise. The movement of the fluid sweeps biological material, such as, for example, blood and tissue, away from the tip to reduce a build-up of embolic material on or adjacent to the tip.

In another aspect, tip 20 further includes at least one cooling chamber configured for cooling hotspots associated with conventional ablation catheters. While previous efforts to control the temperature of ablation catheters and to reduce impedance rise have focused on the distal-most outer surface of the catheter, other areas of the tip or electrode can also exhibit unwanted temperature rise. In one aspect, a proximal cooling chamber is positioned within tip 20 for cooling. The cooling chamber can receive a flow of fluid to draw heat away form the proximal portion of the electrode, such as, for example, a portion of the tip adjacent to the catheter body where RF current tends to concentrate.

In one embodiment, tip 20 comprises a body 41 having a fluid passage therethrough. Body 41 can be constructed of one or more segments that are detachably or fixedly mated with one another and together define the fluid passageway. In one aspect, body 41 includes a sidewall 64 defining an outer surface 43. An insert or inserts can be mated therein to define the fluid passageways. The tip can alternatively be constructed of a single unibody structure in which fluid passageways, including cooling chambers, are formed. Regardless of its construction, body 41 can be formed of a variety of electrically and/or thermally conductive materials including, for example, platinum, iridium, stainless steel, gold, plated brass, and combinations thereof.

Figure 2A:
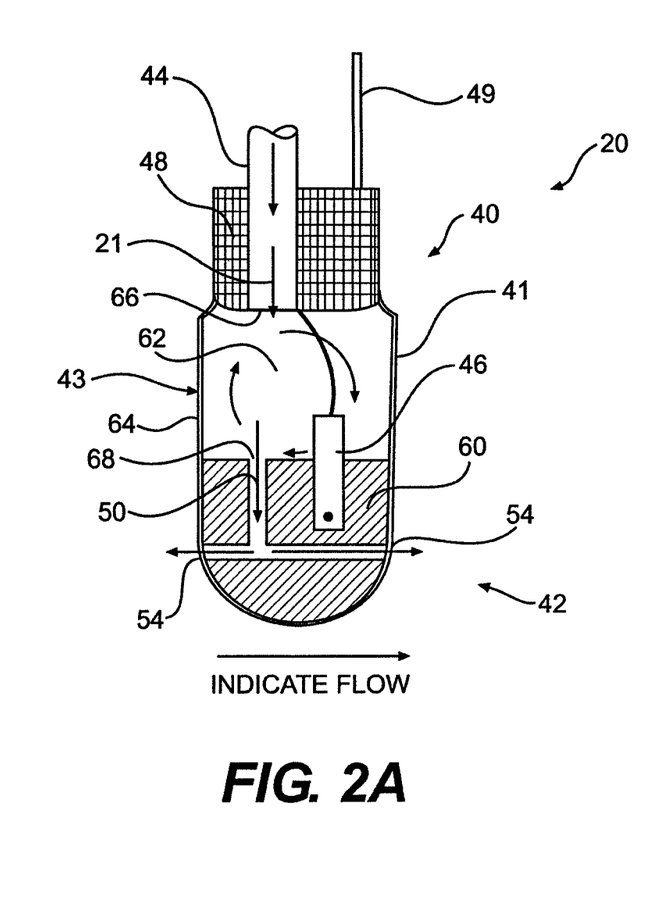
FIG. 2A is a longitudinal cross-sectional view of one embodiment of an electrode tip described herein.
Figure 2B:
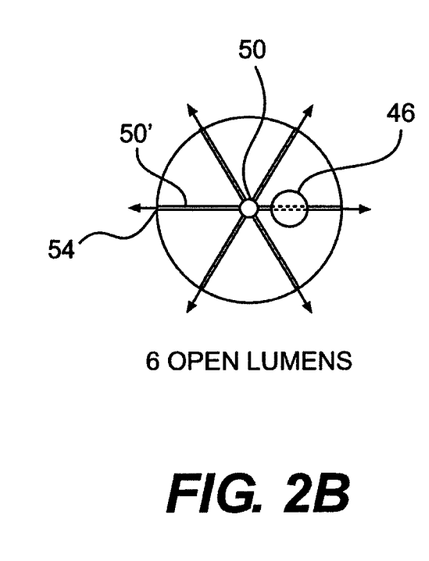
FIG. 2B is a transverse cross-sectional view of the electrode tip of FIG. 2A.

FIGS. 2A and 2B illustrate one embodiment of tip 20 having a proximal end 40 and a distal end 42. The proximal portion of the tip can mate with a catheter body 12. In one aspect, proximal portion 40 includes an area of reduced diameter or width for receipt within a portion of the catheter body. An inner surface of the catheter body wall can surround and mate with the outer surface of body 41 at the area of reduced diameter. Alternatively, the tip and catheter body could mate in a but end connection, the tip could be positioned within a sidewall of the catheter body, and/or the tip could extend around a portion of the outer surface of the catheter body. One skilled in the art will appreciate that a variety of mating mechanism, including a frictional, mechanical, and/or adhesive engagement are considered.

The proximal portion of tip 20 can mate with various lumens, wires, and/or control mechanisms extending through body 12. In one aspect, a fluid lumen 44 extends through proximal portion 40 of tip 20. The fluid lumen can be in fluid communication with a fluid lumen in catheter body 12. In one aspect, a tubular body extends from body 12 into tip 20. Alternatively, the fluid lumen of tip 20 can be defined by a channel with within tip 20, such as, for example, within reinforcing member 48. In another aspect, multiple fluid lumen can extend into and/or through the proximal portion 40 of tip 20.

Where the catheter includes an articulating region, control wires (e.g., push/pull wires) can be mate with tip 20. In one aspect, the proximal portion 40 of the tip includes a reinforcing or anchor member 48 positioned within tip 20. The reinforcing member can be defined by a distinct structure mated within outer wall 64 of the tip body 41. Alternatively, the tip and reinforcing member can have a unibody configuration. In one exemplary aspect, reinforcing member 48 is defined by a stainless steel insert mated with the body 41 of tip 20. Control wire 49 can mate with reinforcing member 48 to anchor the distal end of the control wire. However, such wires can alternatively, or additionally, be fixed at a more proximal location of device 10.

In another aspect, electrically conductive wires can extend through the proximal portion of tip 20 to deliver energy and/or to permit communication with a sensor 46 positioned within tip 20. In one aspect, sensor 46 is a temperature sensor defined by, for example, a thermocouple or thermistor.

The body 41 of tip 20 can further include a thermal or electrode mass 60 positioned within tip 20 and a proximal cooling chamber 62. Cooling chamber 62 is positioned proximal to at least a portion of the thermal mass 60 and/or adjacent to the proximal portion of tip 20. As ablation energy moves through tip 20, areas of increased current density can develop and result in localized hotspots. The device 10 described herein can reduce the effect of proximal hotspots through the use of a proximal cooling chamber. As cooling fluid moves through tip 20, the cooling chamber can represent an area of increased volume relative to a fluid pathway 50 through mass 60. Cooling fluid can circulate through the cooling chamber before exiting through fluid pathway 50 in mass 60. As the cooling fluid passes, it can absorb heat and reduce the effect of localized hotspots.

In one aspect, cooling chamber 62 extends across the majority of the width of the tip proximal to mass 60. In another aspect, the cooling chamber extends between sidewalls 64. Cooling fluid moving through the cooling chamber can draw heat from sidewalls 64 of tip 20, from mass 60 (e.g., the proximal surface thereof), and/or from other portions of body 41 of tip 20. Cooling fluid then moves through thermal mass 60 and fluid pathway 50. In one aspect, fluid ultimately flows in one direction, proximal to distal, through the cooling chamber. However, within the cooling chamber cooling fluid can circulate to absorb heat.

Mass 60 can define a portion of a cooling fluid flow path 50 between a proximal cooling chamber 62 and the point of egress of cooling fluid from tip 20. In one aspect, mass 60 is defined by electrically conductive materials and/or thermally conductive materials, examples of which include, brass, copper, stainless steel, and combinations thereof. In another aspect, mass 60 is defined by a thermally conductive material, but not necessarily an electrically conductive material.

As illustrated in FIGS. 2A and 2B, a temperature sensor 46 can be positioned within mass 60. In one aspect, the thermal conductivity of the mass facilitates temperature sensing while sensor 46 is positioned within mass 60. For example, mass 60 can provide little or no thermal insulation, such that the temperature of the outer surface of the tip is substantially equal to the temperature of the sensor.

In one aspect, mass 60 is comprised of the same material as a sidewall 64 of body 41 and/or is formed of unibody construction. Alternatively, all or a portion of mass 60 can be defined by a separate structure and can mate with sidewall 64. The concept of a sidewall and mass 60 may be discussed as separate elements for the sake of convenience and/or clarity, but such a description does not limit the tip, as described and/or claimed, to a configuration in which the thermal mass is a distinct structure mated with the sidewall. In addition, the outer surface of the thermal mass can define a portion of the outer surface of the tip. For example, the sidewall can define the outer surface of the tip adjacent to a portion of a cooling chamber, while the outer surface of the thermal mass can define a different portion of the outer surface of the tip.

As mentioned above, mass 60 can include at least one fluid passageway 50 therethrough. In one aspect, mass 60 is formed of generally fluid impervious materials and the size and shape of fluid passageway(s) 50 defines the flow rate of cooling fluid through tip 20. Thus, mass 60 can extend across substantially the whole width of tip with the exception of a fluid pathway or pathways.

Heat transfer between tip 20 and fluid within the cooling chamber can be enhanced in several ways. In one aspect, the configuration of the cooling chamber and/or fluid inlet/outlet of the cooling chamber directs fluid circulation within the cooling chamber. For example, cooling chamber 62 can have a larger cross-section area than lumen 44 and/or fluid pathway 50. As fluid enters the cooling chamber, the increased cross-section causes the fluid to circulate with the chamber before exiting. To enhance this effect, the fluid inlet and outlet of the cooling chamber can be offset from one another. As illustrated in FIG. 2, fluid ingress 66 from lumen 44 is offset laterally or radially from fluid egress 68 into fluid pathway 50. As a result, fluid tends to circulate through the cooling chamber as it moves through the cooling chamber. Additional features such as, baffles (not illustrated), can also or alternatively be placed with the cooling chamber and/or in adjacent fluid lumens. In yet another aspect, the fluid ingress and/or egress of chamber 62 can facilitate fluid circulation by directing the cooling fluid at an angle with respect to the longitudinal axis of tip 20 and/or device 10. The angle of the inlet and/or outlet can direct fluid in a swirling motion to increase heat transfer.

The fluid pressure profile of tip 20 can additionally or alternatively assists with heat transfer. In one aspect, the relative size of the cooling chamber with respect to the fluid passageway through the thermal mass provides an increase in fluid pressure within fluid passageway 50. The cooling chamber can have a size (e.g., cross-sectional area) that is larger than the cross-sectional area of the fluid outlet from the cooling chamber and/or larger than the cross-sectional area of the fluid flow path 50 through the thermal mass. This size differential can increase fluid pressure down stream of the cooling chamber. For example, the fluid pressure can be higher in the fluid passageway through the thermal mass compared to the fluid pressure in the proximal cooling chamber. The pressure differential can facilitate circulation of fluid within the cooling chamber and/or assist with heat transfer between the cooling fluid and the thermal mass.

Turning now to the distal portion 42 of tip 20, device 10 can include fluid egress for delivery cooling fluid to an area adjacent to the outer surface of the tip. In particular, device 10 can have an open-loop configuration in which cooling fluid exits the device through tip 20. In one aspect, the distal portion of tip 20 include at least one irrigation aperture 54 for delivery cooling fluid to the tissue/tip interface. For example, FIG. 2B illustrates a cut-away view of tip 20 with fluid passageway 50 extending to six irrigation apertures 54. In one aspect, fluid passageway 50 splits into multiple branches 50' to connect to the irrigation apertures. However, multiple passageway 50 could connect to multiple apertures 54 and/or branches 50' could feed multiple apertures. The exact number of irrigation apertures and the size (i.e., cross-sectional area/width) of the fluid passageway(s) 50 and branches 50' can be chosen based on the desired flow rate, flow pressure, and distribution of cooling fluid.

In one embodiment, the fluid path branches 50' and the irrigation apertures direct cooling flow in a direction substantially orthogonal to a longitudinal axis of the catheter body 12 and/or tip 20. In use, the cooling fluid can flow out of apertures 54 and swirl around tip 20 to reduce coagulation formation and/or to reduce blood concentration adjacent to tip 20. In another aspect, fluid path branches 50' and/or apertures 54 direct fluid flow at an angle in the range of about +/−30 and 90 degrees, +/−45 and 90 degrees, or +/−60 and 90 degrees with respect to the longitudinal axis of the catheter body and/or tip. In another aspect, fluid flow can be directed along a direction co-linear or co-axial to the longitudinal axis of the tip or catheter body. In addition, while coplanar fluid flow branches 50' and apertures 54 are illustrated, a non-coplanar configuration is also contemplated.

In one aspect, irrigation apertures 54 are positioned such that as tip 20 is moved into tissue, the apertures can be positioned below the tissue surface. For example, tip 20 can ablate tissue to a depth greater than the longitudinal spacing between the distal-most surface of the tip and the irrigation apertures. As cooling fluid exits the apertures, the adjacent tissue can direct cooling fluid around the outer surface of the tip to reduce the build-up of biological materials on the tip and/or to dilute the concentration of biological materials in the fluid surrounding the tip.

Irrigation apertures 54 and pathways 50' can be formed in a variety of ways. In one aspect, channels are drilled through sidewall 64 and/or mass 60. While a macroporous tip 20 is illustrated in the Figures, microporous structures are also contemplated. For example, the sidewall 64 and/or mass 60 could be formed from sintered material have a porosity which allows cooling fluid flow therethrough. One skilled in the art will appreciate that the variety of conventional macro and/or microporous catheter materials can be utilized to form tip 20.

Figure 3:
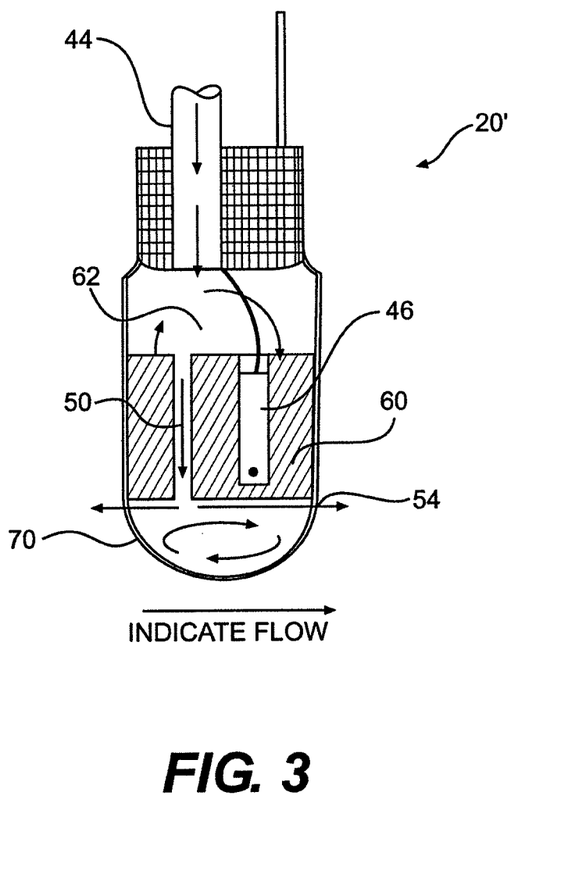
FIG. 3 is a cross-sectional view of another embodiment of an electrode tip described herein.

FIG. 3 is a cross-sectional view of another embodiment of device 10 where thermal mass 60 is spaced from the distal-most end of tip 20'. In use, spacing of the thermal mass can reduce heat transfer to adjacent tissue. A further reduction is heat transfer can be achieved with a distal cooling chamber 70. In one aspect, thermal mass 60 is spaced from the distal most end of tip 20' and cooling chamber 70 is positioned therebetween. Cooling fluid can flow through proximal cooling chamber 62, through thermal mass 60, and into distal cooling chamber 70 before exiting irrigation holes within tip 20'.

In one aspect, the distal cooling chamber can extend across the full width of body 41. For example, distal cooling chamber 70 can extend between the inner surfaces of sidewall 64. In addition, or alternatively, the distal cooling chamber can extend between the distal-most surface of thermal mass 60 and the distal, inner surface of sidewall 64. However, one skilled in the art will appreciate that the length and width of distal cooling chamber 70 can vary depending on the intended use of device 20', the amount of cooling fluid passed therethrough, the desired temperature of the distal tip, and/or the amount of energy delivered via tip 20. In addition, baffles and/or partitions can occupy a portion of the distal cooling chamber.

In one aspect, irrigation apertures 54 extend through the sidewall of body 41 proximate to distal cooling chamber 70. For example, cooling fluid can flow from the distal cooling chamber directly into irrigation apertures 54.

In one aspect, the distal cooling chamber can be adapted to circulate cooling fluid therethrough to increase heat transfer between an inner surface of tip 20 and the cooling fluid. In one aspect, the volume of the distal cooling chamber relative to the fluid passageway 50 facilitates fluid circulation. The relatively smaller cross-sectional area of the fluid passageway through the thermal mass 60 (measured, for example, at the outlet to the distal cooling chamber) compared with a larger cross-section and/volume of the distal cooling chamber provides a pressure drop between fluid passageway 50 and distal cooling chamber 70. The pressure drop increases the speed of the fluid entering the distal cooling chamber and facilitate mixing and/or circulation within the distal cooling chamber.

In addition, or alternatively, in the illustrated embodiment, the fluid inlet and outlet of the distal cooling chamber are not co-linear to encourage cooling fluid movement within the distal cooling chamber. With respect to FIG. 3, cooling fluid can enter the distal cooling chamber along an axis parallel to the longitudinal axis of the tip and can exit the distal cooling chamber via an orthogonal axis.

In one embodiment, the pressure profile of tip 20' includes an increase in pressure in pathway 50 compared to both the proximal and distal cooling chambers. For example, the pressure in the fluid pathway (or pathways) through the thermal mass can be in the range of about 2 to 20 times the pressure measured in the proximal and/or distal cooling chamber. In another aspect, the pressure in the fluid passageway 50 is about 5 to 10 times greater than the pressure in the proximal and/or distal cooling chamber. In yet another aspect, the pressure in the fluid passageway through the thermal mass is in the range of about 40 and 60 psi, while the pressure in the proximal chamber can be in the range of about 6 and 10 psi and the pressure in the distal cooling chamber can be in the range of about 4 and 6 psi. The higher pressure in the fluid passageway(s) through the thermal mass can facilitate heat transfer in the proximal and distal cooling chambers.

The pressure within the distal cooling chamber 70 can also, or alternatively, be chosen to select the desired exit speed of the cooling fluid from the irrigation apertures. In one aspect, the pressure in the distal cooling chamber and the size, shape, and number of irrigation aperture can be selected to provide a fluid exit velocity from the irrigation apertures in the range of about 50 and 700 inches/second.

Figure 4:
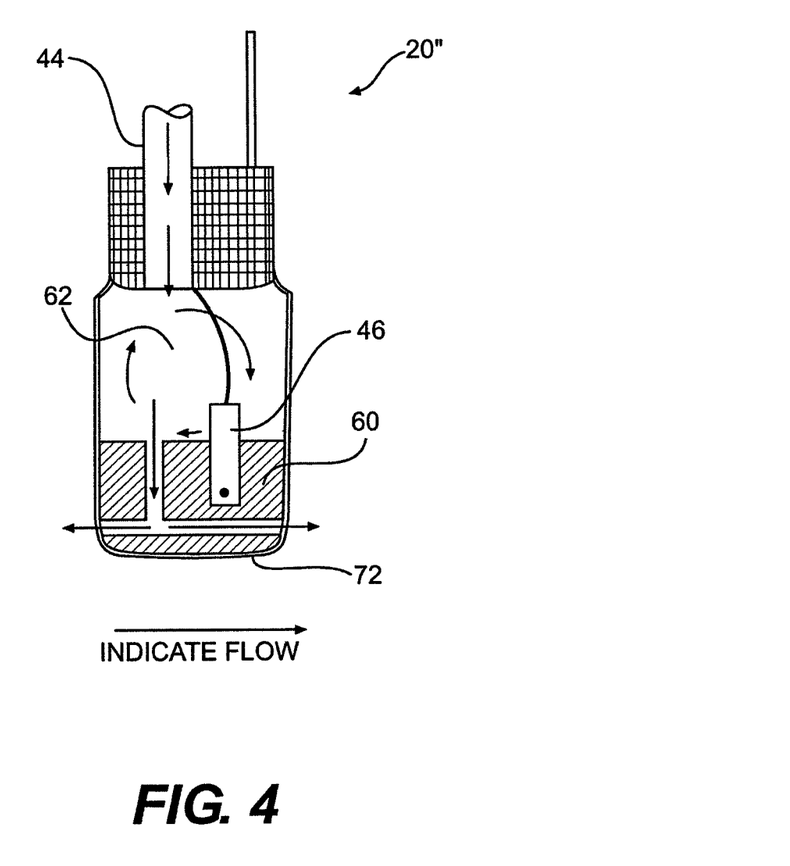
FIG. 4 is a cross-sectional view of yet another embodiment of an electrode tip described herein.

FIG. 4 illustrates another embodiment of the ablating catheter tip. Tip 20" includes a blunt distal end with fluid pathway(s) 50 positioned adjacent to a distal most outer surface 72 of the tip. Tip 20" provides a reduce thermal mass 60 between the cooling fluid pathways and the distal most end of the tip such that the temperature of the tissue contact surface is reduced by the presence of cooling fluid and/or reduced thermal mass present at the distal-most end of the tip (as compared, for example, to tip 20 of FIG. 2A). The size (lateral width and/or longitudinal height) of the fluid pathway(s) adjacent to the distal most surface, the number of fluid pathway branches 50', and/or the fluid flow rate can be variety to control heat transfer between surface 72 and tissue. One skilled in the art will appreciate that the shape of the distal-most portion of the catheter 20 can be varied according to the use of device 10 and the tip described with respect to FIG. 4 is one exemplary embodiment that can be substituted for the distal-most portion of the other catheter tips described herein.

Figure 5:
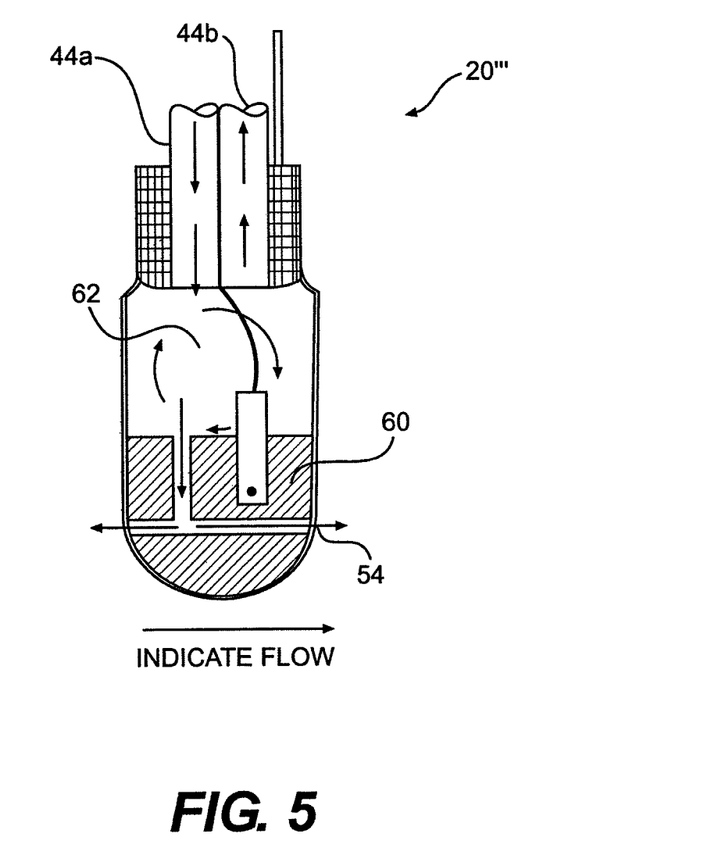
FIG. 5 is a cross-sectional view of still another embodiment of an electrode tip described herein.
Figure 6:
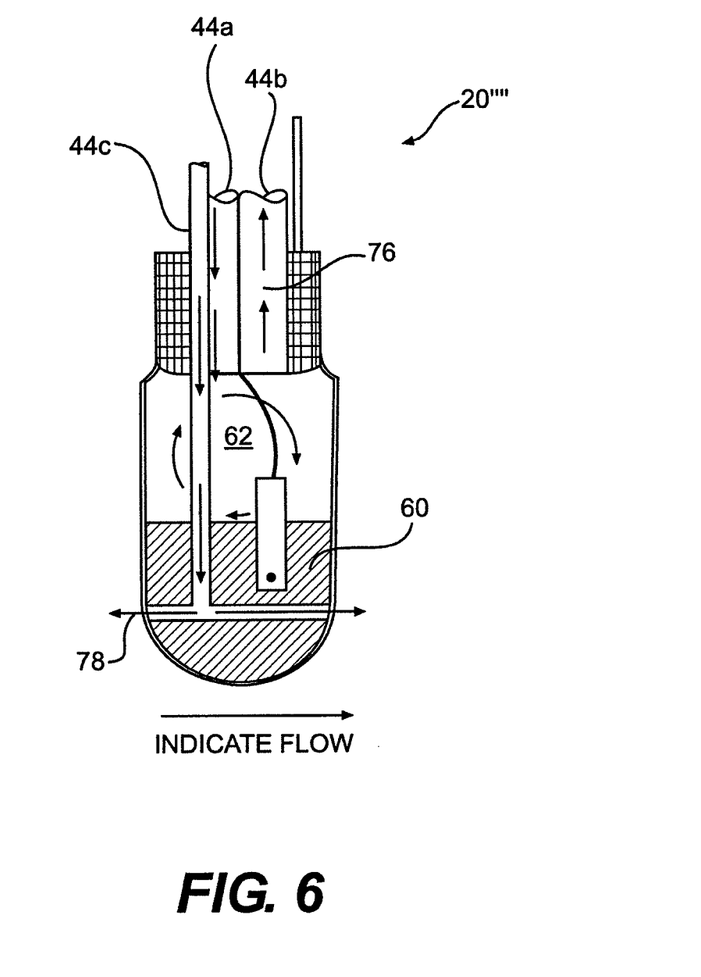
FIG. 6 is a cross-sectional view of another embodiment of an electrode tip described herein.

FIGS. 5 and 6 illustrate yet another embodiment of an ablation catheter tip described herein. Generally, the catheter tips 20, 20', 20" described above have an open loop configuration where fluid flows from the catheter body 12 through the tip and out through irrigation apertures. Conversely, the tip of FIGS. 5 and 6 includes a lumen for the withdrawal of at least a portion of the cooling fluid from the tip. The closed loop or partially closed loop flow path eliminates or reduces the delivery of cooling fluid to the exterior surface of the electrode tip. For example, with respect to FIG. 5, first and second fluid lumens 44a, 44b are in fluid communication with tip 20'''. Lumen 44a can deliver a cooling fluid into, for example, proximal cooling chamber 62. At least a portion of the cooling fluid can then continue on a path as described with respect to FIGS. 2A through 4 above. However, tip 20''' includes a second fluid lumen 44b for removing cooling fluid after the cooling fluid has absorbed heat within the proximal cooling chamber. The second fluid lumen can return the heated fluid to catheter body 12 for egress from device 10 through a proximal location (e.g., handle 22). As a result, heat is removed from tip 20''' through more than one cooling fluid flow path.

Partially closed-loop cooling allows the fluid flow rate into tip 20''' to exceed the fluid flow rate exiting irrigation apertures 54. Accordingly, the amount of fluid circulating through proximal cooling chamber 62 can be increased without requiring a corresponding increase in the fluid flow rate into a patient. Since it is generally preferred to avoid excessive saline delivery during cardiac ablation, the use of both open and closed loop cooling flow paths can allow increased cooling without a corresponding increase in cooling fluid delivered into a patient.

While no distal cooling chamber is illustrated in FIG. 5, a closed loop or partially closed loop cooling flow path could similarly or alternatively withdraw cooling fluid from a distal cooling chamber. In one such exemplary embodiment, second fluid lumen 44b could extend to a distal cooling chamber.

In another embodiment, the electrode tip can include both opening loop cooling and fully closed loop cooling. FIG. 6 illustrates one exemplary embodiment of tip 20'''' having two separate fluid flow paths. The first, path 76 is a closed loop flow path that delivers fluid to and withdraws fluid from a cooling chamber, such as, for example, cooling chamber 62. First fluid path 76 can include first and second fluid lumens 44a, 44b extending through catheter body 12 and into tip 20''''. The cooling fluid enters cooling chamber 62, circulates therein, and absorbs heat. The cooling fluid is then withdrawn through lumen 44b and can exit the catheter.

Fluid path 78, conversely, is an open loop fluid flow path in which the cooling fluid travels through catheter 12 and is delivered to the exterior of tip 20''''. In one aspect, flow path 78 includes a lumen 44c extending between the proximal portion of tip 20'''' and irrigation apertures 54. In one aspect, flow path 78 provides minimal impact on cooling of the tip as fluid travels through path 78 through the tip. Instead, the fluid of flow path 78 provides reduced coagulation formation on the outer surface of the tip.

Alternatively, flow path 78 can extend through mass 60 and flow through a distal cooling chamber (not illustrated) prior to exiting tip 20''''. For example, tip 20'''' could include a distal chamber similar to distal cooling chamber 70 into which cooling fluid flows prior to exiting the ablation catheter.

Regardless of the configuration of the open and closed loop flow path, the presence of two separate flow paths can allow independent control of flow rates and/or cooling fluid pressures. For example, the closed loop fluid pressure could be higher than the open loop fluid pressure in tip 20''''. In addition, different cooling fluids can be used in the different flow paths.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A catheter device, comprising:
   a catheter sized and shaped for vascular access and including an elongate body extending between a proximal end and a distal end and having at least one inner fluid lumen,
   an electrode tip positioned proximate to the distal end of the catheter body, the electrode tip including an outer wall, a physical barrier extending substantially across the entire cross-section of the electrode tip throughout the length of the physical barrier and having at least one fluid passageway therethrough, a cooling chamber configured to receive a cooling fluid from the inner fluid lumen of the elongate body and positioned proximally of the physical barrier and adapted to cool a portion of the electrode tip proximal of the physical barrier, the electrode tip further comprising multiple irrigation apertures in fluid communication with the fluid passageway in the physical barrier, wherein the fluid passageway is spaced apart from the outer wall by a portion of the physical barrier, wherein the entire electrode tip is a single unibody structure made of a single material.

2. The device of claim 1, wherein the cooling chamber extends across substantially the entire width of the electrode tip between the outer walls of the electrode tip.

3. The device of claim 1, wherein the physical barrier is a thermal mass including a material having a high thermal conductivity.

4. The device of claim 1, wherein a temperature sensor is positioned at least partially within the physical barrier.

5. The device of claim 4, wherein at least one of the multiple irrigation apertures is positioned distally of the temperature sensor.

6. The device of claim 1, further comprising a second cooling chamber positioned distally from the physical barrier.

7. The device of claim 1, wherein the fluid passageway through the physical barrier is sized and shaped to produce an increase in the fluid pressure within the fluid passageway through the physical barrier with respect to the cooling chamber.

8. The device of claim 1, wherein a fluid ingress to the cooling chamber is offset from a fluid egress of the cooling chamber.

9. The device of claim 1, wherein at least some of the multiple irrigation apertures are positioned distally with respect to the cooling chamber.

10. A catheter device, comprising:
    a catheter sized and shaped for vascular access and including an elongate body extending between a proximal end and a distal end and having at least one inner fluid lumen,
    an electrode tip positioned proximate to the distal end of the catheter body, the electrode tip including an outer wall, a physical barrier extending substantially across the entire cross-section of the electrode tip throughout the length of the physical barrier and having at least one fluid passageway therethrough, a first cooling chamber configured to receive a cooling fluid from the inner fluid lumen of the elongate body and positioned proximally of the physical barrier and adapted to cool a portion of the electrode tip proximal of the physical barrier, and a second cooling chamber positioned distally of the physical barrier, the electrode tip further comprising multiple irrigation apertures extending through the outer wall, wherein all of the multiple irrigation apertures are positioned at a proximal end of the second cooling chamber such that the second cooling chamber extends distally of all of the multiple irrigation apertures, wherein the fluid passageway is spaced apart from the outer wall by a portion of the physical barrier, wherein the entire electrode tip is a single unibody structure made of a single material.

* * * * *